US010392671B2

(12) United States Patent
Schook et al.

(10) Patent No.: US 10,392,671 B2
(45) Date of Patent: Aug. 27, 2019

(54) METHOD AND REAGENTS FOR DETECTING WATER CONTAMINATION

(71) Applicant: Dow Global Technologies LLC, Midland, MI (US)

(72) Inventors: Paul O. Schook, Lake Zurich, IL (US); Bei Yin, Phoenixville, PA (US)

(73) Assignee: Dow Global Technologies LLC, Midland, MI (US)

(*) Notice: Subject to any disclaimer, the term of this patent is extended or adjusted under 35 U.S.C. 154(b) by 48 days.

(21) Appl. No.: 15/320,978

(22) PCT Filed: Jun. 24, 2015

(86) PCT No.: PCT/US2015/037329
§ 371 (c)(1),
(2) Date: Dec. 21, 2016

(87) PCT Pub. No.: WO2016/028384
PCT Pub. Date: Feb. 25, 2016

(65) Prior Publication Data

US 2017/0283861 A1 Oct. 5, 2017

Related U.S. Application Data

(60) Provisional application No. 62/018,834, filed on Jun. 30, 2014.

(51) Int. Cl.

| | |
|---|---|
| ***C12Q 1/68*** | (2018.01) |
| ***C07H 21/02*** | (2006.01) |
| ***C07H 21/04*** | (2006.01) |
| ***C12Q 1/689*** | (2018.01) |
| ***C12Q 1/6851*** | (2018.01) |
| ***C12Q 1/6848*** | (2018.01) |

(52) U.S. Cl.
CPC ........... *C12Q 1/689* (2013.01); *C12Q 1/6848* (2013.01); *C12Q 1/6851* (2013.01); *C12Q 2600/158* (2013.01); *Y02A 50/451* (2018.01)

(58) Field of Classification Search
None
See application file for complete search history.

(56) References Cited

U.S. PATENT DOCUMENTS

| | | | | |
|---|---|---|---|---|
| 5,468,613 | A * | 11/1995 | Erlich | C07K 14/70539 435/194 |
| 2004/0029129 | A1 | 2/2004 | Wang et al. | |
| 2006/0210967 | A1 | 9/2006 | Agan et al. | |
| 2009/0170717 | A1 | 7/2009 | Agan et al. | |
| 2010/0216141 | A1* | 8/2010 | Bungo | C12Q 1/689 435/6.15 |
| 2011/0059865 | A1* | 3/2011 | Smith | B01J 19/0046 506/16 |
| 2012/0171661 | A1 | 7/2012 | Reidt | |

FOREIGN PATENT DOCUMENTS

| | | | |
|---|---|---|---|
| DE | 4419294 | A1 | 12/1995 |
| JP | 2009039046 | A | 2/2009 |
| WO | WO2002/077183 | A1 | 10/2002 |

OTHER PUBLICATIONS

Gene Bank Accession No. M76178.1. NCBI Database (National Center for Biotechnology Information, Natioinal Library of Medicine (Bethesda, MD, USA), Apr. 26, 1993, available via URL: < ncbi.nlm.nih.gov/nuccore/M76178.1/>.*

Mitsuhashi et al Journal of Laboratory Analysis. 1996. 10: 285-293.*

Bereschenko, L. A et al., "Molecular characterization of the bacterial communities in the different compartments of a full-scale reverse-osmosis water purification plant", Appl Environ Microbiol, (Jul. 2008), vol. 74, No. 17, pp. 5297-5304.

EBI Database accession No. GSN:ACA37193 (Mar. 2008).

Eichler, S. et al., "Composition and dynamics of bacterial communities of a drinking water supply system as assessed by RNA- and DNA-based 16S rRNA gene fingerprinting", Appl Environ Microbiol, (2006), vol. 72, No. 3, pp. 1858-1872.

Gaia, Valeria et al, Consensus Sequence-based scheme for epidemiological typing of clinical and environmental isolates. J. Clin. Microbio., 43(5):2047-2052 (May 2005).

Kwon, S. et al., "Pyrosequencing demonstrated complex microbial communities in a membrane filtration system for a drinking water treatment plant", Microbes Environ, (2011), vol. 26, No. 2, pp. 149-155.

Mentasti M; Fry NK, European Working Group for Legionella Infections Sequence-Based Typing (SBT) Protocol for Epidemiological Typing of Legionella Pneumophila, (Oct. 2009), pp. 1-9, URL: http://www.hpabloinformatics.org.uk/legionella/legionella_sbt/php/SBT%20protocol%20for%20website%202008%20v4.2.pdf.

Reidt, U et al, Automated Immunomagnetic Processing and Separation of Legionella pneumophila With Manual Detection by Sandwich ELISA and PCR Amplification of the ompS Gene, J. Laboratory Automation, 16(2):157-164 (Apr. 2011).

(Continued)

*Primary Examiner* — Carla J Myers
(74) *Attorney, Agent, or Firm* — Howson & Howson LLP; Mary E. Bak

(57) ABSTRACT

A method of examining a water supply for microbial contamination involves contacting a water supply with a novel reagent having high specificity for a *Legionella* microbial species, wherein said reagent does not cross-react, or minimally cross-reacts, with a microbial species other than *Legionella*. The method further involves detecting, or measuring, a contaminating concentration of a *Legionella* species in the water supply. Useful reagents comprise at least one nucleotide sequence primer comprising a primer sequence selected from SEQ ID NO: 3-10 or a combination of such primer sequences. The increased specificity of such reagents permits more sensitive detection of microbial contamination.

11 Claims, No Drawings

Specification includes a Sequence Listing.

(56) References Cited

OTHER PUBLICATIONS

Starnbach, MN et al., Species-specific detectcion of Legionella Pneumophila in water by DNA amplification and hybridization., J. Clin. Microbio., 27(6):1257-1261 (Jun. 1989).
Vekens, E. et al., "Sequence-based typing of Legionella pneumophila serogroup 1 clinical isolates from Belgium between 2000 and 2010", Euro Surveill, (Oct. 2012), vol. 17, No. 43.
Weissenmayer, B. A., "Sequencing illustrates the transcriptional response of Legionella pneumophila during infection and identifies seventy novel small non-coding RNAs", PLOS ONE, (Mar. 2011), vol. 6, No. 3, p. E17570.
Zuo, Z et al, A pathway-based gene signature correlates with therapeutic response in adult patients with Philadelphia chromosome-positive acute lymphoblastic leukemia, Modern Pathology, Aug. 2010, 23:1524-1534.
International Search Report in corresponding International Patent Application No. PCT/US2015/037329.
Written Opinion in corresponding International Patent Application No. PCT/US2015/037329.
International Preliminary Report on Patentability in corresponding International Patent Application No. PCT/US2015/037329.
EPO Communication pursuant to Art 94(3)EPC, dated May 28, 2018 in corresponding EP Patent Application No. EP15736104.9.
Japanese Office Action, Notification of Reason for Refusal, in Applicant's corresponding Japanese Application No. 2016-575516, dated May 9, 2019.
English Translation of Japanese Office Action, Notification of Reason for Refusal, in Applicant's corresponding Japanese Application No. 2016-575516.
English Translation of text of JP2009039046 (A), excluding tables and figures.

* cited by examiner

METHOD AND REAGENTS FOR DETECTING WATER CONTAMINATION

BACKGROUND OF THE INVENTION

*Legionella pneumophila* is a ubiquitous bacterium associated with fresh water. This microorganism can cause a potentially fatal pneumonia, i.e., Legionnaire's Disease, pneumonia, Pontiac fever, if inhaled; and thus is a serious problem for owners, operators, and treaters of domestic water systems, including operators of public facilities which provide water, such as hotels and restaurants, etc. While outbreaks of *L. pneumophila* infection associated with cooling water systems are rarer than outbreaks linked to domestic water systems, such as fountains and HVAC-related components, the ability of cooling towers to spread water droplets contaminated with *L. pneumophila* can cause an outbreak that covers a wide geographical area.

To provide guidance to owners, operators, and treaters of cooling systems various guidelines, codes of practices, and regulations have been put into place globally to detect and/or control the spread of *Legionella* in water sources. In North America, there are two guidelines written by industry groups that are soon to be finalized—the ASHRAE 188P and the CTI STD-159 standard. In addition, OSHA has recommended action levels for remediation and treatment based on counts of *Legionella* found in either domestic or industrial water systems.

The ability to identify and/or quantitatively identify *Legionella* from a mixed microbial population in a water source is critical to determine the potential for infections and to determine if the current treatment protocol is effective at either preventing or remediating *Legionella* in any water system. The US CDC has recommended a culture-based test approach that leverages the acid-tolerance of *Legionella*, a distinctive colony morphology, inherent resistance to the antibiotics glycine, vancomycin, polymixin B and cyclohexamide and the absolute requirements of addition iron and L-cysteine in growth media to successfully enrich *Legionella* bacteria from a mixed culture. However, *Legionella* is also a relatively slow-growing organism that requires 2-10 days under optimal growth conditions to appear on growth media. Given the complex media requirements to successfully isolate *Legionella* and the relatively lengthy incubation time needed for each growth step, this method for detecting *Legionella* is not optimal.

Other detection technologies take advantage of unique *Legionella* outer membrane proteins. A latex agglutination method by Oxoid Ltd, United Kingdom is a tool for confirming that a *Legionella* colony is in fact *L. pneumophila* SG1, the strain most linked to *Legionella* outbreaks. Other methods such as Biotica's LEGIPID™ test and Hydrosense's colorimetric antibody test, which has been marketed by Nalco as the Fastpath Duo System, are relatively rapid antibody-based detection methods for *Legionella* in water. For a direct visualization of *Legionella* in water there are fluorescent antibodies that delineate *Legionella* by serogroup 1 and 2-14/15/16 that can be used with a fluorescent microscope. A limitation of these methodologies and devices is that they require proteins to detect *Legionella*. As proteins can exist in water after cell death, these methods can result in false positive detections.

SUMMARY OF THE INVENTION

In one aspect, a method of examining a water supply for microbial contamination is described which employs novel sensitive reagents having high specificity for a *Legionella* microbial species. This method employs reagents that do not cross-react, or minimally cross-reacts, with a microbial species other than *Legionella*. The method involves contacting a water supply with the reagent and detecting, or measuring, a contaminating concentration of a *Legionella* species in the water supply. In one embodiment, the method employs PCR or qPCR steps including annealing a reagent primer or a combination of primers to a targeted nucleic acid sequence present in *Legionella* at a selected annealing temperature. In another embodiment, the method employs hybridization based steps. The method permits the determination of whether *Legionella* concentration is within acceptable safety limits.

In another aspect, a novel reagent having high specificity for a *Legionella* microbial species, e.g., *L. pneumophila*, and which does not cross-react, or minimally cross-reacts, with a microbial species other than *Legionella* is provided. In one embodiment, the reagent comprises nucleotide primers, such as qPCR or PCR primers, with high specificity for multiple *Legionella* species, but not for *Pseudomonas* species. In another embodiment, the reagent includes a substrate upon which one or more of the nucleotide sequences are immobilized or fixed. In another embodiment, the reagent is a biosensor containing primers identified herein.

In yet another embodiment, a kit comprising one or more of the novel reagents described herein and other assay method components including labels, substrates, a label component capable of interacting with the label and generating a detectable signal, is provided.

Other aspects and advantages of these methods and compositions are described further in the following detailed description.

DETAILED DESCRIPTION OF THE INVENTION

As described herein, novel compositions, e.g., reagents, and methods are provided that enable a fast and accurate detection of microbial contamination of *Legionella*, e.g., *Legionella pneumophila*, in water samples or supplies. As demonstrated in the examples below, the compositions (reagents and primers) and methods described herein provide an improvement in detection methods and compositions which have been used for *Legionella* detection. The reagents and primers described herein are highly specific to *Legionella*, and employ target sequences largely overlooked relative to more common detection genes such as mip or dot/icm. These primers are employed in methods of detection of contamination that employ qPCR-based detection of *Legionella* species, preferably *L. pneumophila* species, PCR and hybridization-based methodologies. The methods and the primers used therein allow lower temperatures to be employed in primer annealing, which provides efficiencies in energy use during performance of the methods. Further the reagents and methods described herein have less cross-reactivity against high levels of contaminating DNA, e.g., *Pseudomonas*, which is common in water systems, and these methods and compositions thereby accomplish the detection of *Legionella* contamination with less false positive results.

A. Definitions and Components of the Methods and Compositions

By the term "water supply" or "samples" as used herein is meant any naturally occurring bodies of water, e.g., lakes, streams, rivers, or industrial or domestic artificial container or body carrying water, e.g., reservoirs, pools, fountains, potable or drinking water, HVAC systems containing or carrying water, bottled water, industrial water supplies or containers, waste water containers, etc. These water supplies or samples can contain purely *Legionella*, a mixed population of microbial organisms with high *Legionella* levels, a mixed population of microbial organisms with low *Legionella* levels, a mixed population of microbial organisms with no *Legionella*, or no microbial contamination. Such samples or water supplies can contain unconcentrated or concentrated DNA samples of a target sequence from the indicated microorganism.

By "target" is meant a nucleic acid sequence that is found in one or more *Legionella* species and has certain desirable characteristics. Such characteristics include relatively stable expression at relatively high levels compared to other *Legionella* gene sequences. Another characteristic is that the nucleotide sequence expression is insensitive to growth conditions and sufficiently unique to *Legionella* to prevent detection of non-*Legionella* microorganisms. The target sequence may be found in nucleic acid materials from the *Legionella* microorganisms that infect mammalian subjects, e.g., humans, and contaminate water or water supplies. In one embodiment, the target is a sequence encodes portions of the *Legionella* major outer membrane protein. The target is a single-stranded ribonucleic acid sequence, or a single strand of a deoxyribonucleic acid sequence from *Legionella*. Included in this definition are RNA, mRNA, microRNA, a single strand of DNA, cDNA, small-interfering RNA (siRNA), short-hairpin RNA (shRNA), peptide nucleic acid (PNA), transfer RNA (tRNA), ribosomal RNA (rRNA) and DNA from a *Legionella* gene. In one embodiment, the selected target gene is known as the major outer membrane protein gene of *Legionella*, or ompS, omp28, lpg1974 or lpnomp28. In one embodiment, the target, ompS, is a gene that appears to be stably expressed regardless of growth condition and is heavily conserved within the *Legionella* genus, making it an appealing target for detection of water supply contamination. The nucleotide sequence of the ompS gene can be found in the Genbank database at accession No. M76178. See also, SEQ ID NO: 17. This target gene also includes the mompS or major outer membrane protein precursor gene, the sequences of which is publically available in the Genbank database at accession No. AF078147.

More specifically, the target of the ompS sequences may be nucleic acid regions of SEQ ID NO: 17, or a homolog or naturally occurring ortholog of same that provides a suitable "target" for detection by a nucleic-acid based detection tool, such as qPCR primers, PCR primers or hybridization probes. For ease of use in identifying target regions of ompS, this specification will refer to regions of SEQ ID NO: 17. However, it is understood by one of skill in the art that homologous sequences of *Legionella* ompS genes having modifications or mutations from the sequence of SEQ ID NO: 17 or from other *Legionella* species ompS are also included in the descriptions of the reagents and methods herein.

By "*Legionella*" is meant any species of the genus *Legionella*, particularly those species commonly found in bodies of water or water supplies. *Legionella* species include without limitation, *L. pneumophila, L. dumoffii, L. longbeachae, L. cherrii, L. pneumophila* SG6A, *L. pneumophila* SG6B, *L. feelei* or combinations thereof. It is a goal of the reagents and methods described herein to detect contaminating *L. pneumophila*, among other species, because it causes human disease.

The term "reagent" as used herein can refer to a single primer, one or multiple sets of forward and reverse primers, labeled primers, primers immobilized on a substrate or in an array or microarray, or devices incorporating any of the above for use in detecting Legionalla contamination in various water supplies.

The term "primer" as used herein is intended to mean oligonucleotide sequences that can bind to and amplify the target sequence in the performance of PCR or qPCR. In one embodiment, a primer set comprises a forward primer that binds to the coding strand of the target in the 5' to 3' direction. In another embodiment, a primer set comprises a reverse primer that binds to the complement of the target sequence in the 3' to 5' direction. As used herein the primers may be about 15 to about 50 nucleotides in length, including any intermediate length in-between, including at least 15, 16, 17, 18, 19, 20, 21, 22, 23, 24, 25, 26, 27, 28, 29, 30, 31, 32, 33, 34, 35, 36, 37, 39, 40, 41, 42, 43, 44, 45, 46, 47, 48, 49 or 50 nucleotides in length. Such primers may be employed in solution, e.g., in buffer, or immobilized on a substrate or microarray. In other embodiment, the primers may be labeled with detectable, e.g., fluorescent, labels, e.g., according to the TaqMan® methodology so that the target-specific oligonucleotides produce a fluorescent signal only when the target DNA is amplified during qPCR, or using fluorescent or other labels such as SYBR® Green I dye.

The term "microarray" refers to an ordered arrangement of hybridizable array elements. In one embodiment, a microarray comprises polynucleotide probes that hybridize to the specified target sequence, on a substrate. In another embodiment, a microarray comprises multiple primers (reverse and forward), optionally immobilized on a substrate.

The term "PCR array" refers to microfluidics card or multiwell plate containing an ordered arrangement of gene-specific forward and reverse primers and fluorescence-labeled probe in each micro-well. This array is used with the sample from the water supply, or a product derived therefrom (e.g., cDNA or cRNA derived from RNA) in real-time PCR reactions which are monitored using fluorescent dye, for example SYBR Green or Taqman technology using a reporter fluorescent dye. Each set of primers is designed to amplify the target sequence of interest, such as those described herein. Such primers can readily be designed by one of skill in the art using known techniques, given the instructions on the primer identities described in this specification. See e.g., reference 13. Primers may also be prepared or available commercially, for example from Invitrogen: bioinfo.invitrogen.com/genome-database/browse/gene-expression/keyword/Taqman%20primers?ICID=uc-gex-Taqman.

The term "real-time quantitative PCR", or "qPCR" refers to a technique combining PCR amplification and detection into a single step. With qPCR, fluorescent dyes are used to label PCR products during thermal cycling. Real-time PCR instruments measure the accumulation of fluorescent signal during the exponential phase of the reaction for fast, precise quantification of PCR products and objective data analysis. qPCR reaction products are fluorescently labeled using one of two main strategies: Reactions are run in real-time PCR instruments with thermal cycling and fluorescence detection capabilities. By using highly efficient PCR primers and optimal conditions for amplification, every target molecule is copied once at each cycle and data are captured throughout the thermal cycling. Since qPCR reactions are set up with a large molar excess of PCR primers and thermostable DNA polymerase, in the early rounds of thermal cycling, target-template is the limiting factor for the reaction thus, fluorescent signal is directly proportional to the amount of target in the input sample.

B. Reagents of the Invention

In one embodiment, a reagent for examining a water supply for microbial contamination has high specificity for a *Legionella* microbial species, and does not cross-react, or minimally cross-reacts, with a microbial species other than *Legionella*. In one embodiment, such a reagent comprises at least one nucleotide sequence primer (DNA or RNA) that amplifies or hybridizes to a target sequence in *Legionella*. In another embodiment the target sequence is found between and including nucleotides 528 and 844 of SEQ ID NO: 17. In one embodiment, the ompS target sequence is found between and including nucleotides 327 and 491 of SEQ ID NO: 17. In another embodiment the target sequence is found between and including nucleotides 327 and 844 of SEQ ID NO: 17. In another embodiment the target sequence is found between and including nucleotides 327 and 491 of SEQ ID NO: 17. In another embodiment the target sequence is found between and including nucleotides 327 and 550 of SEQ ID NO: 17. In another embodiment the target sequence is found between and including nucleotides 327 and 680 of SEQ ID NO: 17. In another embodiment the target sequence is found between and including nucleotides 528 and 550 of SEQ ID NO: 17. In another embodiment the target sequence is found between and including nucleotides 528 and 680 of SEQ ID NO: 17. In another embodiment the target sequence is found between and including nucleotides 660 and 844 of SEQ ID NO: 17. In another embodiment the target sequence is found between and including nucleotides 660 and 680 of SEQ ID NO: 17. In still other embodiments, the target regions may include those regions identified above including from about 5 to about 15 additional nucleotides on either end of the identified sequences.

These reagents may be primers as defined above which are selected from the forward primer sequences set out in Table 1 below as SEQ ID NOs: 1, 3, 4, 5 and 6. It should be understood that these sequences may differ from those of Table 1 by certain modifications. In one embodiment, a modification is indicated by the presence of the indicated wobble bases shown and defined in Table 1. Other modifications of the primer sequences of Table include primer sequences that differ from those of Table 1 by including from 1 to about 5 additional contiguous nucleotides 5' to the 5' nucleotide base of each forward primer location in SEQ ID NO: 17. In another embodiment additional modified primer sequences may differ from those of Table 1 by including from 1 to about 5 additional contiguous nucleotides 3' to the 3' nucleotide base of each forward primer located in SEQ ID NO: 17. The primers may be modified by adding contiguous bases to either end of the identified primer, or deleting one or more bases from either end of the primer, or a combination of both types of modifications. In yet a further embodiment, a primer may differ from a sequence of Table 1, by deleting 1, 2, 3, 4, or 5 bases from the 5' or 3' end of the related sequence in Table 1 and adding 1, 2, 3, 4, or 5 additional contiguous bases to the opposite end of the primer, thus shifting the primer sequence. For example, one primer sequence could be a modification of SEQ ID NO:4 and span nucleotides 526 to 550 of SEQ ID NO: 17 or 526 to 547 of SEQ ID NO: 17 and so on.

These reagents may be primers as defined above which are selected from the reverse primer sequences set out in Table 1 below as SEQ ID NOs: 2, 7, 8, 9, 10. It should be understood that these sequences may differ from those of Table 1 by modifications such as the indicated wobble bases in that table. As described above, additional modifications can result in modified reverse primer sequences that differ from those of Table 1 by including from 1 to about 5 additional contiguous nucleotides 5' to the 5' nucleotide base of each reverse primer in SEQ ID NO: 17. In another embodiment additional reverse primer sequences may differ from those of Table 1 by including from 1 to about 5 additional contiguous nucleotides 3' to the 3' nucleotide base of each reverse primer in SEQ ID NO: 17. In a manner analogous to that described above for the forward primers, the reverse primers of Table 1 may be modified by shifting the primer sequence 1 to 5 bases 5' or 3' from the primers position on SEQ ID NO: 17.

Thus, in one embodiment, the reagent comprises a set of primers comprising a forward nucleotide sequence primer and a reverse nucleotide sequence primer selected from Table 1. In one embodiment, the reagent contains a forward primer comprising at least one of SEQ ID NO: 1, 3, 4, 5 or 6 and the reverse primer comprises at least one of SEQ ID NO: 2, 7, 8, 9, or 10. In another embodiment, the reagent contains the forward primer comprising SEQ ID NO: 4 and the reverse primer comprising one of SEQ ID NO: 8, 9 or 10. In another embodiment, the reagent contains the forward primer comprising SEQ ID NO: 4 and the reverse primer comprising SEQ ID NO: 10. In another embodiment, the reagent contains the forward primer comprising SEQ ID NO: 4 and the reverse primer comprising one of SEQ ID NO: 8. In another embodiment, the reagent contains the forward primer comprising SEQ ID NO: 4 and the reverse primer comprising one of SEQ ID NO: 9. In a similar manner, the reagent may comprise other combinations of the forward and reverse primers of Table 1, SEQ ID NOs: 1-10. In still another embodiment, the reagent comprises multiple sets of reagents selected from the primers comprising SEQ ID NOs: 1-10 or 3-10. In still another embodiment, the reagent comprises all nucleotide sequence primers selected from primer sequences comprising SEQ ID NO: 1-10, or sequences having modifications thereof on the 5' or 3' ends as described above.

In still another embodiment, a reagent comprises a substrate upon which one or more of the nucleotide sequences are immobilized or fixed. Such a substrate is an array, a microarray, a microchip, a plastic surface, or a glass surface. Association of the primer on the substrate and methods for accomplishing the association are well known in the art. Alternatively, the primer sequences may be provided in a suitable buffer depending upon the type of method in which the reagent is to be used.

In still another embodiment, the reagent includes a primer to which a detectable label or label component is associated. Suitable detectable labels include fluorescent labels such as those employed by the TAQMAN reagents, or other known fluorescent molecules. Suitable labels may be selected from among many known label types by one of skill in the art given the teachings of this specification.

In yet another embodiment, a reagent of this invention can be in the form of a kit containing one or more of the primers, reverse and forward primer sets or labeled primer-probes, suitable labels and labeling methodologies, suitable substrates, and/or label component, e.g., enzymes, capable of interacting with the label associated with a primer and generating a detectable signal.

In yet another embodiment, the reagent is configured as a water monitoring device comprising the primers described herein.

C. Methods of Detecting Contamination

The reagents, e.g., primers described herein, are desirably used in methods for *Legionella* detection involving the techniques of polymerase chain reaction (PCR), quantitative PCR (qPCR), or oligonucleotide hybridization-based methodologies.

In one aspect, a method of examining a water supply for microbial contamination, particularly contamination with *Legionella*, is provided. Such a method involves contacting a water supply with a reagent having high specificity for a *Legionella* microbial species, wherein the reagent does not cross-react, or minimally cross-reacts, with a microbial species other than *Legionella*. Thereafter, the method involves detecting, or measuring, a contaminating concentration of a *Legionella* species in the water supply.

In one embodiment, the reagent employed in the method is one of the reagents described herein. For example, the method can employ a reagent comprising at least one nucleotide sequence primer selected from:

(a) forward primer sequence 327 comprising SEQ ID NO: 3

(b) forward primer sequence 528 comprising SEQ ID NO: 4

(c) forward primer sequence 660 comprising SEQ ID NO: 5;

(d) forward primer sequence 825 comprising SEQ ID NO: 6

(e) reverse primer sequence GC-327 comprising SEQ ID NO: 7;

(f) reverse primer sequence GC-528 comprising SEQ ID NO: 8

(g) reverse primer sequence GC-660 comprising SEQ ID NO: 9;

(h) reverse primer sequence GC-825 comprising SEQ ID NO: 10; or (i) a combination of primer sequences comprising (a) through (h) or (j) modifications of such primer sequences with wobble bases or by adding or deleting one or more 5' or 3' bases or by shifting the position of the primer 1 to 5 bases along its position in SEQ ID NO: 17.

In another embodiment, the method employs multiple sets of reagents selected from the primers of (a) through (j), or includes multiple steps using some or all of the primers or reverse/forward primer pairs in a suitable methodology. Any of the reagents described above are believed to be useful in the methods described below and in the examples.

Thus, in one embodiment, the method involves performing PCR or qPCR steps to amplify the target sequence by annealing a primer or a combination of primers to the targeted nucleic acid sequence present in *Legionella* at a selected annealing temperature. In one embodiment, the annealing temperature is less than 58° C. In another embodiment, the annealing temperature is about 40° C. In another embodiment, the annealing temperature is about 41° C. In another embodiment, the annealing temperature is at least 40, 41, 42, 43, 44, 45, 46, 47, 48, 49, or 50° C. In still other embodiments, the annealing temperature of the reagents described herein is lower than the annealing temperatures employed by use of other known ompS primers. For example, as shown in Table 2, the method can involve contacting a sample with 1 μM primer for 3 min at 95° C.; and performing 35 cycles of denaturation for 30 sec at 94° C.; annealing the primers for 30 sec at 40° C.; elongation for 30 sec at 72° C.; and a 10 min 72° C. extension step. Still other conditions are described in detail in the examples below.

In another embodiment, the measuring comprises hybridizing a primer to a targeted nucleic acid sequence present in *Legionella* and performing a polymerase chain reaction (PCR) or a quantitative polymerase chain reaction (qPCR). These methods employ amplifying the targeted sequence and determining whether said *Legionella* concentration is within acceptable safety limits.

A variety of methods of measuring or detecting the amount of contamination are known in the art once the primers have amplified the target sequence or identified in by hybridization. Methods of detecting can include running the amplified or hybridized target sequences on with agarose gel for visualization. Running electric current through the gel causes the negatively-charged DNA to migrate to positively charged side of gel. The gel is stained with dye that binds to double-stranded DNA, thereby allowing visualization. The larger the DNA, the slower it moves through the gel. Still other methods of measuring the results of PCR and hybridization methodologies can be selected by one of skill in the art.

Thus, in one embodiment, the methods employ a reagent with high specificity for multiple *Legionella pneumophila* only. Thus, in one embodiment, the method and reagents can distinguish between contamination of a water supply with *Legionella* from contamination with a *Pseudomonas* species, such as *Pseudomonas aeruginosa* or *Pseudomonas denitrificans*.

As demonstrated in the examples below, the primers described herein provide a higher degree of target specificity in qPCR and PCR methodologies. The examples showed testing against purified DNA from various strains, and testing against DNA extracted from six CDC ELITE testing samples. As discussed below, primers 528/825gc are better than the known SEQ ID NO: 15 and 16 primer sequences described in US patent publication No. 20120171661 because they have decreased cross-reactivity with other species of microorganism. These qPCR primers, e.g., SEQ ID NO: 1 and 2 or 4 and 10 allow for faster detection of *Legionella* than the primers disclosed in other known assays, such as that of US patent publication No. 2012071661.

In order to further understand the above-described device and to demonstrate how the method may be carried out in practice, certain embodiments will now be described with reference to the accompanying drawings above and the examples described below. The following examples are provided for illustration and do not limit the disclosure or scope of the claims and specification.

EXAMPLE 1

Identification of Target DNA and Assays Used

The inventors a *Legionella* gene identified as lpg1974 (Weissenmayer, Prendergast et al. 2011) as a source of a suitable target for novel *Legionella* detection reagents. This gene, also known as ompS (NCBI Genbank Accession No. M76178.1) was found to be fairly stably expressed at relatively high levels to other *Legionella* genes. Thus, this gene and its encoding outer membrane protein met the inventors' twin goals of a nucleotide sequence whose expression would be insensitive to growth conditions and unique to *Legionella* to prevent detection of non-target organisms.

A. Developing and Testing qPCR Primers

Because the 5'end of ompS appeared to be less variable relative to other regions of the gene and appeared to be more specific to *L. pneumophila* organisms, it was targeted for qPCR primer generation. The inventors employed a tool, i.e., the IDT primer design website (http://www.idtdna.com/scitools/Applications/RealTimePCR/) to construct qPCR primers with specific melting temperature, length, and homodimer/heterodimer features (Table 1).

Amplification of target DNA was done under the following conditions:

95° C. for 3 minutes; followed by 41 cycles of: 95° C. for 10 seconds, 58° C. for 10 seconds, 72° C. for 30 seconds; then 95° C. for 10 s, followed by a melt curve using software default conditions. qPCR amplification was done in the CFX96 Bio-Rad System with a commercially purchased *Legionella* genomic standard used for run validation. The qPCR conditions varied from the recommended instructions, but as efficiency and R^2 values were within normal parameters, it is unlikely that the changes had any effect. These conditions involved using per reaction well 12.5 μl Bio-Rad iQ SYBR Master Mix, 0.15 μl of both forward and reverse primer (stock primer concentration was 50 μM), and 4.7 μl molecular-biology grade $H_2O$ (instead of the correct 7.2 μl $H_2O$). To that volume 5 μl of 1/100 diluted purified genomic DNA was added.

B. Developing PCR Primers

Regions of DNA that could be used either for traditional PCR approaches or a hybridization-based approach were also analyzed for a broader detection, e.g., of multiple *Legionella* species. To do this, the DNA sequence of the ompS gene from *L. pneumophila* and the ompS gene from *L. longbeachae* were aligned and directly compared to identify regions of total similarity or sufficiently high sequence similarity to permit a primer with 1-2 wobble bases to be identified. "Wobble bases" refer to certain nucleotide bases located in a primer sequence for which alternative base options are possible, based upon the primer pool used in a reaction. For example, a wobble base of "R" would be 50% guanine and 50% cytosine in a given primer pool. This approach allowed for the broadening of a primer reactivity to include highly related but not 100% identical regions of DNA.

The ompS alignment was visually examined to identify 4 regions of DNA that could be used for primers, with complementary primers generated so that key regions could be used for different tests. The primers identified in Table 1 below, were tested using a traditional PCR 2× Master Mix (Promega) with the following conditions: 12.5 μl Master Mix, 0.5 μl of both forward and reverse primers, and 9.5 μl $dH_2O$. To this, 2 μl of purified genomic DNA isolated using the MolBio Ultraclean DNA Isolation Kit was added. The PCR conditions in the initial screen were as follows: 2 min at 95° C., 35 cycles of: 30 s at 95° C., 30 s at 45° C. (40° C. for primers 528 SEQ ID NO: 4 and 825Gc SEQ ID NO: 10 due to primer melting temperature requirements), and 30 s at 72° C.; then 10 min at 72° C. for a final extension step.

The primer sequences SEQ ID NO: 1-10 and known sequences SEQ ID NO: 15 and 16 identified in Table 1 are located on the ompS gene.

TABLE 1

PRIMER SEQUENCES AND NAMES

| Inventor's Primer Sequences | Sequence[4] | Target | Appln | SEQ ID # |
|---|---|---|---|---|
| Legionella OmpS Set 3 Forward | GCA GTG CTT TGT TTG CAG GTA CGA | ompS | qPCR | 1 |
| Legionella OmpS Set 3 Reverse | ATG CCA ATT TCT CCA GCC ACC AAC | ompS | qPCR | 2 |
| OmpS 327F | TTT GCA GGT ACS ATG GGT CCA GT | ompS | PCR | 3 |
| OmpS 528F | GAA GGT TCT TAT CAC TTC AAC AC | ompS | PCR | 4 |
| OmpS 660F | GAA MTG GGK CAA TTY GTT GAT | ompS | PCR | 5 |
| OmpS 825F | ATG AAY TAT GTA TTY GGT AA | ompS | PCR | 6 |
| GC-OmpS 327F[5] | ACT GGA CCC ATS GTA CCT GCA AA | ompS | PCR | 7 |
| GC-OmpS 528F[5] | GTG TTG AAG TGA TAA GAA CCT TC | ompS | PCR | 8 |
| GC-OmpS 660F[5] | ATC AAC RAA TTG MCC CAK TTC | ompS | PCR | 9 |
| GC-OmpS 825F[5] | TTA CCR AAT ACA TAR TTC AT | ompS | PCR | 10 |
| Primer Sequences obtained from other publications | | | | |
| mompS-492F[1] | GACATCAATGTGAAC TGG | mompS | PCR | 11 |
| mompS-1116R[1] | TGGATAAATTATCCA GCCGGACTTC | mompS | PCR | 12 |
| mompS-450F[2] | TTG ACC ATG AGT GGG ATT GG | mompS | PCR | 13 |
| mompS-1126R[2] | TGG ATA AAT TAT CCA GCC GGA CTT C | mompS | PCR | 14 |
| US20120171661F[3] | gcg gct gta ttt gct ctg gga a | ompS | PCR | 15 |
| US20120171661R[3] | taa gcc tat gta ggg gcc aga tgc | ompS | PCR | 16 |

[1]Source is reference no. 11.
[2]Source is reference no. 10
[3]Source is reference no. 8.
[4]Nucleic acid "wobble base" abbreviations include S representing either C or G; M representing either A or C; Y representing either C or T; R representing either A or G; and K representing either G or T.
[5]The "gc" on the primer name refers to "generated complement", where the primer manufacturer (IDT) generated a primer that was located on the same location on the opposite strand of DNA so that the same region of DNA could be tested with primers both 5' and 3' to its location.

C. Initial Primer Comparison

A series of benchmarking of known primers was conducted to identify whether the novel ompS primers demonstrated an improvement when compared with other known ompS primers. In one comparison at conditions that were best suited for the primer setup (2° C. below the primer melting temperature (TM), the reaction conditions were 12.5 μl Master Mix, 0.5 μl of both forward and reverse primers, and 10.5 μl $dH_2O$ where 1 μl of purified genomic DNA isolated using the MolBio Ultraclean DNA Isolation Kit was added. DNA from defined strains and from nucleic acid isolated from a CDC ELITE testing panel were assayed.

D. Refined Primer Comparison

Cell suspensions from defined bacterial species (*Legionella pneumophila* ATCC BAA74, P. *Pseudomonas aeruginosa* ATCC 15442, *Burkolderia cepacia* ATCC 25416,

*Sphingomonas paucimobilis* BAA1092, *Flavobacterium odoratum* (aka *Myroides odoratus*) NCIMB 13294, *Enterobacter aerogenes* ATCC 13048, and *Klebsiella pneumonia* ATCC 8308) were obtained and split into two aliquots. One aliquot was plated to obtain a cfu/ml count as a measure of organism concentration and the other was subjected to DNA isolation via the MolBio UltraClean DNA Kit. Once the cfu/ml of each starting colony was identified, each DNA vial was assigned an equivalent genomic unit/ml concentration based on the cell counts. From that, a dilution range was generated to simulate absence of target organism, then increasing amounts of *Legionella* relative to a high level of non-target organism DNA (see conditions specified in Table 2).

qPCR-based method for broad *Legionella* detection. DNA from liquid culture-grown *P. aeruginosa* and *P. denitrificans* was used as negative controls. DNA from *L. pneumophila* BAA74 served as a positive control, with DNA extracted from strains isolated from CDC ELITE test samples (*L. dumoffii, L. longbeachae, L. feelei*, and *L. cherii*) used as experimental samples. To obtain *Legionella* DNA, colonies were swabbed from bacterial media plates and agitated into water within a biosafety cabinet for extraction using the MoBio Ultraclean DNA extraction kit. DNA was diluted 1/100 in $dH_2O$ prior to analysis and with plastic reagents from Bio-Rad used in the qPCR run. Commercially purchased *L. pneumophila* genomic standards served as the material for the 5-log standard dilutions.

TABLE 2

PRIMER EXPERIMENTAL CONDITIONS

| Test | Primer Sequences | Target | Rxn Mix | PCR Cycle Conditions (DNA in water; mimics low concentration samples) |
|---|---|---|---|---|
| qPCR test | SEQ ID NOs: 1 and 2 | ompS | qPCR | 0.333 μM primer (ideally 0.3 μM); 95° C. for 3 min, 41 cycles of denaturation for 10 sec at 95° C.; annealing for 10 sec at 58° C.; elongation for 30 sec at 72° C.; 10 sec at 95° C.; a melt curve analysis SYBR green detection |
| Primer Conditions | SEQ ID NOs: 4 and 10 | ompS | PCR | 1 μM primer, 3 min at 95° C.; 35 cycles of denaturation for 30 sec at 94° C.; annealing for 30 sec at 40° C.; elongation for 30 sec at 72° C.; 10 min 72° C. extension step |
| Comparison Test 1 | SEQ ID NOs: 11 and 12 | mompS | PCR | 1 μM primer, 35 cycles of denaturation for 30 sec at 94° C.; annealing for 30 sec at 50° C.; elongation for 30 sec at 72° C.; 10 min 72° C. extension step |
| Comparison Test 2 | SEQ ID NOs: 13 and 14 | mompS | PCR | 0.2 μM primer; 35 cycles of denaturation for 30 sec at 95° C.; annealing for 30 sec at 55° C.; elongation for 40 sec at 72° C.; 10 min 72° C. extension step |
| Comparison Test 3 | SEQ ID NOs: 15 and 16 | ompS | PCR | 1 μM primer; 35 cycles of denaturation for 60 sec at 94° C.; annealing for 60 sec at 58° C.; elongation for 90 sec at 72° C.; 10 min 72° C. extension step |

A master block was made with the DNA concentrations so that the same DNA material would be used in each reaction. To confirm that no meaningful changes in the DNA sample or that false-positives occurred from cross-contamination from the start of the reaction to the end, the primers SEQ ID NOs: 1-10 were tested at the beginning and towards the end of the experiment. Primers were tested at the conditions suggested in other publications.

E. DNA Gel Protocol

To visualize PCR fragments either Lonza's Flashgel cassette-based system or a standard operating procedure was followed for gel casting, buffer, and safety considerations. According to the SOP, 5 μl of PCR product/loading dye was added to each well with 5 of 100 bp DNA Ladder (Promega)/loading dye added to the left most well (2 μl for the Lonza Flashgel system). 1.5% agarose gels were run in 1×TBE buffer for 30 minutes at 100V. Then, they were placed into an empty plastic pipette tip box and exposed to 50 ml of 1×SYBR Green (Invitrogen) for approximately 60 minutes, then visualized on the Bio-Rad Gel XR Imager. Lonza Flashgels were operated using manufacturer's instructions and visualized with the built-in imaging camera.

EXAMPLE 2 qPCR-Based Method for Broad *Legionella* Detection qPCR primers SEQ ID NOs. 1 and 2 were generated to determine whether the ompS gene could be used in a Efficiency of the run was 95.7% with an R^2 of 0.999, suggesting that despite a slightly higher concentration of mix and primers, the run was well-within acceptable qPCR norms. *L. pneumophila* and *L. dumoffii* appeared to be preferentially amplified relative to other *Legionella* bacterial samples. Negative controls *P. denitrificans* and a non-template added control failed to have meaningful amplification, with *P. aeruginosa* amplified at $1\times10^1$ cfu/ml range. Given that the cells used in the extraction were straight from late exponential/stationary phase cells, this count is likely not an accurate measurement of *P. aeruginosa* cell presence, but rather indicative of low-level cross contamination. Of particular interest is the high reactivity of *L. dumoffii* with the qPCR ompS primers.

Repetition of this experiment involves normalizing the DNA input following enumeration of live cells to get approximately equivalent genomic units/ml and assist in confirming that this high degree of similarity is accurate.

EXAMPLE 3

Hybridization Method for Broad *Legionella* Detection

Following what observed to be a highly selective *Legionella* primer design and a determination that primers (Table 1) should be spaced further apart for the proposed hybridization approach, new primers were selected from a more central to 3' end of the ompS gene. Specific regions were isolated based on high degree of sequence homology to *L. longbeachae*. The “gc” on the primer name refers to “generated complement”, where the primer manufacturer (IDT) generated a primer that was located on the same location on the opposite strand of DNA so that the same region of DNA could be tested with primers both 5' and 3' to its location. The suitability of each primer set was then tested using the conditions listed in Table 2.

To test these primers, genomic DNA from swabbed *Legionella* strains (or liquid cultures in the case of *P. aeruginosa* and *P. denitrificans*) were assayed with the ompS primers 327, 528, 660, and 825 along with their “gc” counterparts (SEQ ID NOs: 3-10, respectively). The melting temperature for each reaction was 45° C. or 40° C. depending on primer melting temperature requirements. For this initial testing reaction conditions were as follows: 1 μM primer, 3 min 95° C., 35 cycles of denaturation for 30 s at 94° C.; annealing for 30 s at 40° C. or 45° C., and elongation for 30 s at 72° C. with a 10 min 72° C. extension step at the end. The results are displayed as gel images (not shown). A first gel image showed primer 327 vs. 528 GC screening against purified genomic DNA in Lanes identified as A: DNA ladder, B: *L. pneumophila* (contro), C: *Pseudomonas* (negative control); D: *L. dumoffii*; E. *L. longbeachae*; F: *L. cherri*; G: *L. pneumophila* SG6A; H: *L. pneumophila* SG6B and I: *L. feelei*. All species were detected by the primer showing some cross-reactivity. A second gel image showed primer 327 SEQ ID NO: 3 and primer 660 GC SEQ ID NO: 9 screening against purified genomic DNA in Lanes identified as in the first gel image. *L. feelei* was not detected by the primer pair, which showed stronger cross-reactivity. A third gel image of primer 327 SEQ ID NO: 3 vs. 825 GC SEQ ID NO: 10 screening against purified genomic DNA in Lanes identified as in the first gel image. *L. feelei* was not detected by the primer pair, which showed minor cross-reactivity. A fourth gel image showed primer 528 SEQ ID NO: 4 vs 825 GC SEQ ID NO: 10 screening against purified genomic DNA in Lanes identified as in the first gel image. All species were detected. Minor cross reactivity was observed. A fifth gel image showed primer 327 SEQ ID NO: 3 vs. 660 GC SEQ ID NO: 9 screening against purified genomic DNA in Lanes identified as in the first gel image. All species were detected. Minor *Legionella* cross reactivity was observed. No or minimal *Pseudomonas* detection was observed. A sixth gel image showed primer 660 SEQ ID NO: 5 vs 825 GC SEQ ID NO: 10 screening against purified genomic DNA in Lanes identified as in the first gel image. *L. feelei* was not detected. *Legionella* cross reactivity was observed. No or minimal *Pseudomonas* detection was observed.

Given the cleanliness of the reactions, the primer pair 528/825gc SEQ ID NOs: 4 and 10 were selected for additional analysis.

Once these reactions had been done, additional work to compare these primers to other known sequences, e.g., primers SEQ ID NOs: 15 and 16 (ref. 8) were performed to determine whether the primers SEQ ID NO: 4 and 10 provided an improvement in *Legionella* detection. The testing fell within two approaches—testing of primers against purified genomic DNA and testing of mock-samples provided by the US CDC for ELITE certification testing. The results of these tests are displayed as gel images (not shown). A gel image was acquired showing the testing of DNA isolated from CDC-ELITE testing samples with primers 528 SEQ ID NO: 4/825GC SEQ ID NO: 10. The DNA in Lanes was identified as A: DNA marker, B: CDC-ELITE Sample 1, C: CDC-ELITE Sample 1-conc; D: CDC-ELITE Sample 2, E: CDC-ELITE Sample 2-conc; F: CDC-ELITE Sample 3, G: CDC-ELITE Sample 3-conc; H: CDC-ELITE Sample 4, I: CDC-ELITE Sample 4-conc; J; CDC-ELITE Sample 5, K: CDC-ELITE Sample 5-conc; L: CDC-ELITE Sample 6, M: CDC-ELITE Sample 6-conc. Promising results were obtained with unfiltered samples. Background increases with ~200 fold sample concentration. Conclusions from CDC testing of 528/825GC ompS primers SEQ ID NOs: 4 and 10, respectively, are: Pure *L. pneumophila* sg 3, $2.6\times10^3$ cfu/ml; Pure *L. pneumophila* sg 14, $3.3\times10^1$ cfu/ml; Negative for *L. pneumophila*; Negative for *L. pneumophila*; Mixed *L. pneumophila* sg 6, $1.3\times10^3$ cfu/ml; Mixed *L. pneumophila* sg 6, $6.0\times10^1$ cfu/ml. A further gel image showed comparative testing of DNA isolated from CDC-ELITE testing samples with inventors' primers (DMC) and known primers SEQ ID NO: 15 and 16. The DNA in Lanes was identified as A: DNA marker, B: CDC-ELITE Sample 1 DMC, C: CDC-ELITE Sample 1-known; D: CDC-ELITE Sample 2 DMC, E: CDC-ELITE Sample 2-known; F: CDC-ELITE Sample 3 DMC, G: CDC-ELITE Sample 3-known; H: CDC-ELITE Sample 4 DMC, I: CDC-ELITE Sample 4-known; J: CDC-ELITE Sample 5 DMC, K: CDC-ELITE Sample 5-known; L: CDC-ELITE Sample 6 DMC, M: CDC-ELITE Sample 6-known. The results show no meaningful difference with testing samples. Both DMC primers and known primers (derived from U.S. Patent Publication No. 20120171661; SEQ ID NOs: 15 and 16) detect *L. pneumophila* in mixed mock-environmental samples. No improvement was observed. Improvement with the inventors' primers was unclear when assaying the CDC ELITE samples. However, when the same test was run against purified DNA, there was an improvement observed in cross-reactivity. Primers 528 and 825gc showed less cross-reactivity with non-*Legionella* microbial contamination, e.g., *P. aeruginosa*, that the other sequences known in the art. A gel was acquired showing results of comparative testing of DNA isolated from monoculture genomic DNA isolates with DMC primers SEQ ID NO: 4 and 10 and SEQ ID NO: 15 and 16 primers with *P. aeruginosa* as a negative control. Both DMC primers and primers SEQ ID NO: 15 and 16 detect a wide range of *Legionella* species. The DMC primers are less cross-reactive against high levels of contaminating DNA relative to *P. aeruginosa*. A further gel showed comparative testing of DNA isolated from monoculture genomic DNA isolates with DMC primers SEQ ID NOs: 4 and 10, and the known primers SEQ ID NOs: 15 and 16 with *P. dentrificans* as a negative control. 2μl of PCR product was loaded onto a 2.2% Lonza FLASHGEL™ system. The lanes A-K of the gel are as follows: A: DNA ladder, B: *L. pneumophila* (DMC), C: *L. pneumophila* (known); D: *P. denitrificans* (DMC); E: *P. denitrificans* (known); F: *L. dumoffii* (DMC); G: *L. dumoffii* (known); H: *L. longbeachae* (DMC); I: *L. longbeachae* (known); J: *L. feelei* (DMC); and K: *L. feelei* (known). The SEQ ID NO: 4 and 10 PCR primers demonstrate an improvement over known primers. The sequences described herein provide less-cross reactive detention of *Legionella* species under a variety of conditions.

Following this initial screen, the testing protocol was amended. The test concentrations of DNA with the defined genomic DNA may have been too high to accurately determine if there was an improvement with the inventors' primers relative to the primers SEQ ID NOs. 15 and 16. Based on interactions with cooling water services companies and field trial experiences, typical bacterial burden in these samples tended to be around $1\times10^5$ cfu/ml. Second, the primer pool was extended to include two other sets of known primers from references 10 and 11, SEQ ID NOs: 11 through 14 of Table 1. Specific microbial species were tested based on publications (see e.g., refs. 1-3) and discussions with water treatment applications specialists, and availability of these contaminating microbial strains.

A master block of isolated DNA with the equivalent genomic unit/ml to counted cfu/ml was generated as described in Example 1 and used for PCR analysis. The degree to which cross-reactivity was observed in either total non-target samples or samples with a high non-target to *L. pneumophila* DNA ratio was then observed. A gel image (not shown) was obtained providing Omp528/825GC SEQ ID NOs: 4/10 primers showing low-concentration gradient testing against *P. aeruginosa* ATCC 15442. Another gel image was obtained of Omp528/825GC SEQ ID NOs: 4/10 primers showing low-concentration gradient testing against *Burkholderia cepacia* ATCC 25416. Further, low-concentration gradient testing was performed of (1) Omp528/825GC SEQ ID NOs: 4/10 primers against *Sphingomonas paucimobilis* BAA 1092; (2) Omp528/825GC SEQ ID NOs: 4/10 primers against *Enterobacteria aerogenes* ATCC 13048; (3) Omp528/825GC SEQ ID NOs: 4/10 primers against *Klebsiella pneumonia* ATCC 8308; and (4) Omp528/825GC SEQ ID NOs: 4/10 primers against *Klebsiella pneumonia* ATCC 8308. The lanes A-M of these gels are as follows: A: DNA ladder, B: $1\times10^5$ cfu/ml non-target DNA, C: $1\times10^5$ cfu/ml non-target DNA, $1\times10^1$ cfu/ml *L. pneumophila* BAA74 DNA; D: $1\times10^5$ cfu/ml non-target DNA, $1\times10^2$ cfu/ml *L. pneumophila* BAA74 DNA; D: $1\times10^5$ cfu/ml non-target DNA, $1\times10^3$ cfu/ml *L. pneumophila* BAA74 DNA; D: $1\times10^5$ cfu/ml non-target DNA, $1\times10^4$ cfu/ml *L. pneumophila* BAA74 DNA; D: $1\times10^5$ cfu/ml non-target DNA, $1\times10^5$ cfu/ml *L. pneumophila* BAA74 DNA; D: $1\times10^4$ cfu/ml non-target DNA, $1\times10^6$ cfu/ml *L. pneumophila* BAA74 DNA; D: $1\times10^3$ cfu/ml non-target DNA, $1\times10^7$ cfu/ml *L. pneumophila* BAA74 DNA; D: $1\times10^2$ cfu/ml non-target DNA, $1\times10^7$ cfu/ml *L. pneumophila* BAA74 DNA; K: $1\times10^1$ cfu/ml non-target DNA, $1\times10^5$ cfu/ml *L. pneumophila* BAA74 DNA; L: $1\times10^5$ cfu/ml *L. pneumophila* BAA74 DNA; M: No DNA Control. The 528F and 825gc reverse primers were tested at the beginning and end of the experiment to ensure that any cross-reactivity observed with other primers were genuine and not due to inadvertent cross-contamination of material. The first round of primer testing resulted in gels too faint to read clearly. When these tests are repeated, it is anticipated that the results will be consistent with the ones of Omp528/825GC SEQ ID NOs: 4/10 primers against *Klebsiella pneumonia* ATCC 8308 and Omp528/825GC SEQ ID NOs: 4/10 primers against *Klebsiella pneumonia* ATCC 8308.

Interestingly, a non-specific amplification was observed with these primers against *B. cepacia* and *E. aerogenes*. A low-concentration gradient testing was conducted of (A) known 1116R/492 SEQ ID NOs: 12/11 primers against *P. aeruginosa* ATCC 15442; (B) 1116R/492 SEQ ID NOs: 12/11 primers against *Burkholderia cepacia* ATCC 25416. The lanes A-M of the gel are as in the prior paragraph. PCR conditions with 1μM primer, 3 mins. 95C;35X(94C at 30 s, 50C at 30S, 72C 30s and 10 min 72C. A further low-concentration gradient testing was performed of (C) 1116R/492 SEQ ID NOs: 12/11 primers against *Sphingomonas paucimobilis* BAA 1092; (D) 1116R/492 SEQ ID NOs: 12/11 primers against *Enterobacteria aerogenes* ATCC 13048; (E) 1116R/492 SEQ ID NOs: 12/11 primers against *Klebsiella pneumonia* ATCC 8308. The lanes A-M of the gel are as in the prior paragraph.

Additionally, a low-concentration gradient testing of (A) 1126R/450 SEQ ID NOs: 14/13 primers against *P. aeruginosa* ATCC 15442; (B) 1126R/450 SEQ ID NOs: 14/13 primers against *Burkholderia cepacia* ATCC 25416; (C) 1126R/450 SEQ ID NOs: 14/13 primers against *Sphinogomonas paucimobilis* BAA 1092 (See Table 2 for the cycle conditions); and (D) 1126R/450 SEQ ID NOs: 14/13 primers against *E. aerogenes* ATCC 13048. The lanes A-M of the gel are as in the prior paragraphs.

These results immediately suggest that the 528F and 825gc primers constitute an improvement over the known primers. A similar improvement was not observed with the *K. pneumonia* tests.

The known 1126R/450 primers SEQ ID NOs. 14 and 13 were assayed according to the conditions listed in Table 2. Although data on the performance of the 1126R/450 primers against *Klebsiella* were absent, there was not a clear diminution of performance relative to the 528F/825gc primers with the species tested with regards to cross-reactivity. The primers appeared to have a higher threshold for detection ($1\times10^2$-$1\times10^3$) of *Legionella*. Some wells had failure to amplify; therefore this experiment when repeated is anticipated to confirm a detection sensitivity improvement.

Finally, the primers SEQ ID NO: 15 and 16 were tested per conditions in Table 2 to determine performance relative to the inventors' primers.

In summary, while the qualities of gels were initially poor and will be repeated, there was a clear cross-reactivity observed against *B. cepacia*. A low-concentration gradient testing was performed of (A) US20120171661 primers SEQ ID NO: 15 and 16 against *P. aeruginosa* ATCC 15442 (PCR conditions are listed in Table 2); (B); (B) F and R known primers SEQ ID NOs: 15 and 16 against *Burkholderia cepacia* ATC 25416; (C) US20120171661 F and R primers SEQ ID NOs: 15 and 16 against *Sphingomonas paucimobilis* BAA 1092(See Table 2 for the cycle conditions); (D)_US20120171661 F and R primers SEQ ID NOs: 15 and 16 against *E. aerogenes* ATCC 13048; and (E) US20120171661 F and R primers SEQ ID NOs: 15 and 16 against *Klebsiella pneumonia* ATCC 8308. The lanes A-M of the gel are as the prior paragraphs.

Again, this suggests that the DMC primers have an improvement relative to the US20120171661 primers.

However, the present data on these primers provides evidence indicating that the inventor-identified primers constitute an improvement of other ompS or mompS-focused primers for the detection of *Legionella* in a complex sample.

Technical and scientific terms used herein have the same meaning as commonly understood by one of ordinary skill in the art to which this invention belongs and by reference to published texts, which provide one skilled in the art with a general guide to many of the terms used in the present application. Any definitions are provided for clarity only and are not intended to limit the claimed invention.

It should be understood that while various embodiments in the specification are presented using "comprising" language, under various circumstances, a related embodiment is also described using "consisting of" or "consisting essentially of" language. It is to be noted that the term "a" or "an", refers to one or more, for example, "a test compound," is understood to represent one or more test compounds. As such, the terms "a" (or "an"), "one or more," and "at least one" is used interchangeably herein.

Numerous modifications and variations of the embodiments illustrated above are included in this specification and are expected to be obvious to one skilled in the art. Such modifications and alterations to the compositions and processes described herein are believed to be encompassed in the scope of the claims appended hereto. All documents, including patents, patent applications and publications, and non-patent publications listed or referred to above, as well as Sequence Listing, are incorporated herein by reference in their entireties to the extent they are not inconsistent with the explicit teachings of this specification.

References

1. Bereschenko, L. A et al (2008 September). "Molecular characterization of the bacterial communities in the different compartments of a full-scale reverse-osmosis water purification plant." Appl Environ Microbiol 74(17): 5297-5304.

2. Eichler, S., et al, (2006). "Composition and dynamics of bacterial communities of a drinking water supply system as assessed by RNA- and DNA-based 16S rRNA gene fingerprinting." Appl Environ Microbiol 72(3): 1858-1872.

3. Kwon, S., et al, (2011). "Pyrosequencing demonstrated complex microbial communities in a membrane filtration system for a drinking water treatment plant." Microbes Environ 26(2): 149-155.

4. Weissenmayer, B. A., et al (2011). "Sequencing illustrates the transcriptional response of Legionella pneumophila during infection and identifies seventy novel small non-coding RNAs." PloS One 6(3): e17570.

5. US patent publication No. 20040029129

6. US patent publication No. 20060210967

7. US patent publication No. 20090170717

8. US patent publication No. 20120171661

9. German Patent publication No. DE4419294

10. Vekens, E., et al. 2012 Sequence-based typing of *Legionella pneumophila* serogroup 1 clinical isolate from Belgium between 2000 and 2010. Euro Surveill 17(43).

11. Gaia V, et al. Consensus Sequence-Based Scheme for Epidemiological Typing of Clinical and Environmental Isolates of *Legionella pneumophila*. J Clin Microbiol. May 2005;43(5):2047-52.

12. Mentasti M, Fry NK. European Working Group for *Legionella* Infections Sequence-Based Typing (SBT) protocol for epidemiological typing of *Legionella pneumophila*. Version 4.2. October 2009; pp 1-9. Available from: hpabioinformatics.org.uk/legionella/legionella_sbt/php/SBT%20protocol%20for%20website%202008%20v4.2.pdf 13. Zuo et al, Modern Pathology, 2010, 23:524-34

What is claimed is:

1. A reagent for examining a water supply for microbial contamination comprising a nucleotide sequence primer having specificity for a *Legionella* microbial species, wherein said nucleotide sequence primer does not bind, or binds at a detectably reduced level, with a microbial species other than *Legionella* when compared with its binding to said microbial *Legionella* species, wherein said reagent comprises a forward nucleotide sequence primer consisting of SEQ ID NO: 4 and a fluorescent label attached thereto, and a reverse nucleotide sequence primer consisting of SEQ ID NO: 10, or wherein said reagent comprises a forward nucleotide sequence primer consisting of SEQ ID NO: 4, and a reverse nucleotide sequence primer consisting of SEQ ID NO: 10 and a fluorescent label attached thereto.

2. The reagent according to claim 1, further comprising an additional forward nucleotide sequence primer consisting of at least one of SEQ ID NOs: 1, 3, 5 or 6 and an additional reverse nucleotide sequence primer consisting of at least one of SEQ ID NO: 2, 7, 8, or 9.

3. The reagent according to claim 1, wherein the reagent further comprises primers consisting of the sequence of SEQ ID NO: 1, 2, 3, 5, 6, 7 and 9.

4. The reagent according to claim 1, which further comprises a substrate upon which one or more of the nucleotide sequence primers is immobilized or fixed.

5. The reagent according to claim 4, wherein said substrate is an array, a microarray, a microchip, a plastic surface, or a glass surface.

6. A kit comprising the reagent of claim 1 and one or more components selected from a label, a substrate, and a label component capable of interacting with the label and generating a detectable signal.

7. A water monitoring device comprising the reagent of claim 1.

8. A method of examining a water supply for *Legionella* microbial contamination comprising:

contacting a water supply sample with the reagent of claim 1; and detecting or measuring the amount of binding between the reagent and target nucleic acids in the water supply sample to thereby detect or determine a contaminating concentration of a *Legionella* species in the water supply.

9. The method according to claim 8, wherein the detecting or measuring is performed at an annealing temperature lower than 58° C.

10. The method according to claim 8, wherein the detecting or measuring comprises performing a polymerase chain reaction (PCR) or real time qualitative polymerase chain reaction (qPCR).

11. The method according to claim 8, further comprising distinguishing between contamination with *Legionella* species from contamination with a *Pseudomonas* species.

* * * * *

SEQUENCE LISTING

```
<160> NUMBER OF SEQ ID NOS: 17

<210> SEQ ID NO 1
<211> LENGTH: 24
<212> TYPE: DNA
<213> ORGANISM: Legionella pneumophila

<400> SEQUENCE: 1

gcagtgcttt gtttgcaggt acga                                        24


<210> SEQ ID NO 2
<211> LENGTH: 24
<212> TYPE: DNA
<213> ORGANISM: Legionella pneumophila

<400> SEQUENCE: 2

atgccaattt ctccagccac caac                                        24


<210> SEQ ID NO 3
<211> LENGTH: 23
<212> TYPE: DNA
<213> ORGANISM: Legionella pneumophila

<400> SEQUENCE: 3

tttgcaggta csatgggtcc agt                                         23


<210> SEQ ID NO 4
<211> LENGTH: 23
<212> TYPE: DNA
<213> ORGANISM: Legionella pneumophila

<400> SEQUENCE: 4

gaaggttctt atcacttcaa cac                                         23


<210> SEQ ID NO 5
<211> LENGTH: 21
<212> TYPE: DNA
<213> ORGANISM: Legionella pneumophila

<400> SEQUENCE: 5

gaamtgggkc aattygttga t                                           21
```

<210> SEQ ID NO 6
<211> LENGTH: 20
<212> TYPE: DNA
<213> ORGANISM: Legionella pneumophila

<400> SEQUENCE: 6
atgaaytatg tattyggtaa 20

<210> SEQ ID NO 7
<211> LENGTH: 23
<212> TYPE: DNA
<213> ORGANISM: Legionella pneumophila

<400> SEQUENCE: 7
actggaccca tsgtacctgc aaa 23

<210> SEQ ID NO 8
<211> LENGTH: 23
<212> TYPE: DNA
<213> ORGANISM: Legionella pneumophila

<400> SEQUENCE: 8
gtgttgaagt gataagaacc ttc 23

<210> SEQ ID NO 9
<211> LENGTH: 21
<212> TYPE: DNA
<213> ORGANISM: Legionella pneumophila

<400> SEQUENCE: 9
atcaacraat tgmcccaktt c 21

<210> SEQ ID NO 10
<211> LENGTH: 20
<212> TYPE: DNA
<213> ORGANISM: Legionella pneumophila

<400> SEQUENCE: 10
ttaccraata catarttcat 20

<210> SEQ ID NO 11
<211> LENGTH: 18
<212> TYPE: DNA
<213> ORGANISM: Legionella pneumophila

<400> SEQUENCE: 11
gacatcaatg tgaactgg 18

<210> SEQ ID NO 12
<211> LENGTH: 25
<212> TYPE: DNA
<213> ORGANISM: Legionella pneumophila

<400> SEQUENCE: 12
tggataaatt atccagccgg acttc 25

<210> SEQ ID NO 13
<211> LENGTH: 20
<212> TYPE: DNA
<213> ORGANISM: Legionella pneumophila

<400> SEQUENCE: 13
ttgaccatga gtgggattgg 20

<210> SEQ ID NO 14
<211> LENGTH: 25
<212> TYPE: DNA
<213> ORGANISM: Legionella pneumophila

<400> SEQUENCE: 14
tggataaatt atccagccgg acttc 25

<210> SEQ ID NO 15
<211> LENGTH: 22
<212> TYPE: DNA
<213> ORGANISM: Legionella pneumophila

<400> SEQUENCE: 15
gcggctgtat ttgctctggg aa 22

<210> SEQ ID NO 16
<211> LENGTH: 24
<212> TYPE: DNA
<213> ORGANISM: Legionella pneumophila

<400> SEQUENCE: 16
taagcctatg taggggccag atgc 24

<210> SEQ ID NO 17
<211> LENGTH: 1707
<212> TYPE: DNA
<213> ORGANISM: Legionella pneumophila

<400> SEQUENCE: 17
cgaataaatt ttggcgcaaa ttaatagtca tgcactcccc ctcattacta caaaattaaa 60
ggaaaaagca gactacttgc tggcgtataa atcaataaca gcagatactg atcaaatctt 120
acatttaatg tttaaatcaa tgagttaaat aactttaatt taataaaatt acccttatta 180
tttgatgaag aatcaaatag attctgttag aattcgctaa tcctagatgt ttaaaggaat 240
aacaataata aatcagtgga gaacgggata tgtttagttt gaaaaaaaca actgcggctg 300
tatttgctct gggaagcagt gctttgtttg caggtacgat gggtccagta tgtacgccag 360
gcaatgtgac tgttccttgc gaaagaaccg catgggatat tggtattacc gcactttatc 420
tgcagccaac ttatgatgct gattggggct ataatggttt tactgatgtt ggtggctgga 480
gaaattggca tgatgttgat ttagagtggg attggggctt taaattagaa ggttcttatc 540
acttcaacac aggcaatgac atcaacgtca attggtacca tttggatgcc aacaccgatc 600
attgggcgtt tgttgatcaa ttgcacgcct acgatattac ctgggatgca gtgaatgctg 660
aactggggca atttgttgat tttagcgcga acaaaaaaat gcgcttccat ggcggcgttc 720
agtatgccta catcaaaaca gacgttaatc gtcacttaaa cggcttcttt ctagataact 780
tcaattccaa attcaatgga tttggtcccc gtaccggcct tgatatgaat tatgtattcg 840
gtaatgggtt tggtatttat gcaaaatcag ctgtagcaat cctggtcggt acaagcaaat 900
tcgtggataa ctgtactgtc tgtggttttt cttatggctc caaaaatgca atagtgccag 960
aagttgaaat gaagttagga gcagattata cctatgcaat ggctcaaggt gatgtgactc 1020
tggatgtggg ttacatgtgg ttcaattact tcaatgcctt acataatact gctgccgtga 1080
atgttggctt aggcacttct ctggaaaccg acttctctgc atctggcccc tacataggct 1140
taaaatatgt tggcaatgtc taaataaccc caaattatgc tgctaatcta gtcatgatca 1200

-continued

```
agcagcagta tgcaaaaaac ccgtattgac ataggctgct aatacgggtt ttttttattt   1260

ctctctgttt aattaagtta gttatcctat ctaagctaac ttgtaattat atgataattt   1320

cccaatgaaa ttgagataac tttatgcgaa acaataattg gtccgtgttg ggcaacatca   1380

ccaatgaaaa atcacatccg tgatctgctg cgaaaactat agtaaacgca ataatctgct   1440

ggttctgcct gatgcataat tcttttccat tccaaagatc gtgggttata atgaaaccat   1500

ctatcacaaa ccgtttataa aaataaacat gcctgatgtt ctcggcaaac ctgatgcaac   1560

ccagattcca gatgacgtct ggcttgacat tcttatcaat tatcttcaac cacaagatat   1620

tgtaaacctg tctgaaatca acaatcgctt gagcagactt ttcaaaactc aacacactca   1680

atctgagcaa ttgaaccaaa aaaaaaa                                        1707
```